United States Patent [19]
Niimura et al.

[11] Patent Number: 5,635,727
[45] Date of Patent: Jun. 3, 1997

[54] METHOD FOR FORMING NEUTRON IMAGES

[75] Inventors: Nobuo Niimura; Yuuko Karasawa, both of Ibaragi-ken; Kenji Takahashi; Hiroki Saito, both of Kanagawa-ken, all of Japan

[73] Assignees: Fuji Photo Film Co., Ltd., Kanagawa; Japan Atomic Energy Research Institute, Tokyo, both of Japan

[21] Appl. No.: 492,228

[22] Filed: Jun. 19, 1995

[30] Foreign Application Priority Data

Jul. 19, 1994 [JP] Japan ................... 6-166921

[51] Int. Cl.$^6$ ............................................. G01N 23/09
[52] U.S. Cl. ................. 250/583; 250/390.02; 250/484.4; 250/584
[58] Field of Search ................. 250/484.9, 583, 250/390.02, 584, 585, 586

[56] References Cited

U.S. PATENT DOCUMENTS

| | | | |
|---|---|---|---|
| 2,245,787 | 6/1941 | Kallmann et al. | 250/390.02 |
| 2,272,375 | 2/1942 | Kallmann et al. | 250/390.02 |
| 3,859,527 | 1/1975 | Luckey | 250/337 |
| 4,236,078 | 11/1980 | Kotera et al. | 250/484.4 |
| 4,239,968 | 12/1980 | Kotera et al. | 250/484.4 |
| 4,535,246 | 8/1985 | Shani | 250/390.02 |
| B1 4,236,078 | 1/1989 | Kotera et al. | 250/484.4 |

FOREIGN PATENT DOCUMENTS

| | | |
|---|---|---|
| 2928245 | 8/1986 | Germany. |
| 56-116777 | 9/1981 | Japan. |
| 57-23673 | 2/1982 | Japan. |
| 57-23675 | 2/1982 | Japan. |
| 58-69281 | 4/1983 | Japan. |
| 58-206678 | 12/1983 | Japan. |
| 59-27980 | 2/1984 | Japan. |
| 59-47289 | 3/1984 | Japan. |
| 59-56479 | 3/1984 | Japan. |
| 59-56480 | 3/1984 | Japan. |
| 59-75200 | 4/1984 | Japan. |
| 61-28899 | 2/1986 | Japan. |

OTHER PUBLICATIONS

"Shin Hihakai Kensa Benran", (New Non–Destructive Inspection Handbook), published by The Japanese Society For Non–Destructive Inspection, pp. 205–219.

Primary Examiner—Carolyn E. Fields
Attorney, Agent, or Firm—Sughrue, Mion, Zinn, Macpeak & Seas

[57] ABSTRACT

Stimulable phosphor sheets are superposed one upon another. Each stimulable phosphor sheet is provided with a first layer of a substance, which absorbs neutrons and emits secondary particles, and a second layer of a stimulable phosphor, which can store energy from the secondary particles. The stimulable phosphor sheets are exposed to a neutron beam carrying image information, and neutron images are thereby stored on the stimulable phosphor sheets. Image signals representing the neutron images stored on the stimulable phosphor sheets are then obtained. The image signal components of the image signals are then added to each other, which represent corresponding picture elements in the neutron images. An image signal representing the neutron images stored on the stimulable phosphor sheets is thereby obtained. Alternatively, at least one stimulable phosphor sheet for absorbing neutrons, emitting particles, and storing energy of these particles and, a second phosphor sheet for detecting and storing energy from γ-rays, are superposed and exposed to a neutron beam carrying image information. After this exposure, images become stored on each layer of the phosphor sheets. The image signals representing the images stored on each layer are then obtained. The image signal stored in the γ-ray detecting layer is subtracted from the image signal stored on the neutron detecting layer to obtain the neutron image stored on the stimulable phosphor sheets.

11 Claims, 4 Drawing Sheets

METHOD FOR FORMING NEUTRON IMAGES

BACKGROUND OF THE INVENTION

1. Field of the Invention

This invention relates to a method for forming a neutron image with a neutron beam carrying image information of an object or a sample, e.g. a neutron beam, which has passed through the object, or a neutron beam, which has been emitted by the sample. This invention particularly relates to a method for forming a neutron image, wherein a plurality of stimulable phosphor sheets are superposed one upon another and used.

2. Description of the Prior Art

In the field of non-destructive inspections, techniques have heretofore been used wherein radiation images of objects are obtained by utilizing neutrons, which have been produced by nuclear reactors, or the like. Such techniques are described in, for example, "Shin Hihakai Kensa Benran" (New Non-Destructive Inspection Handbook), published by The Japanese Society For Non-Destructive Inspection, pp. 205-219. The techniques comprise the steps of: (a) exposing a metal converter, which has been combined with a photographic film, to a neutron beam, which has passed through an object, or a neutron beam which has been emitted by a sample, the neutrons of the neutron beam being converted by the metal converter into radiation, such as $\alpha$-rays, $\beta$-rays, or $\gamma$-rays, and (b) exposing the photographic film to the resulting radiation, an image carried by the neutron beam being thereby formed as a photographic image. The metal converter is provided with a layer containing a substance, such as gadolinium (Gd) or lithium (Li), which has a large cross section of nuclear reaction. Neutrons are absorbed by the layer and are thereby converted into the secondary particles, such as $\alpha$-particles or $\beta$-particles.

The techniques described above are referred to as the neutron radiography. The neutron radiography has the advantages in that it is possible to obtain radiation images representing image information of moisture, organic substances, or the like, which could not be obtained with the radiography utilizing X-rays or $\gamma$-rays. In addition, nonmetals coexisting with metals can be detected accurately.

A method for forming a neutron image, which method is improved over the neutron radiography described above, is disclosed in, for example, Japanese Unexamined Patent Publication No. 61(1986)-28899. In the disclosed method, instead of the photographic film and the metal converter being used, a stimulable phosphor sheet is utilized. The stimulable phosphor sheet is provided with a layer of a substance, which is capable of absorbing neutrons and emitting secondary particles, and a layer of a stimulable phosphor, which is capable of storing energy from the secondary particles. When the stimulable phosphor sheet is exposed to a neutron beam carrying image information, the layer of the aforesaid substance absorbs neutrons and emits secondary particles. The stimulable phosphor layer of the stimulable phosphor sheet is exposed to the secondary particles and stored energy from the secondary particles. The stimulable phosphor sheet, on which energy from the secondary particles has been stored, is then scanned in two directions with stimulating rays, which have wavelengths falling within the stimulation wavelength range for the stimulable phosphor sheet and which cause the stimulable phosphor sheet to emit light in proportion to the amount of energy stored thereon during its exposure to the neutron beam. The emitted light is detected photoelectrically, and an image signal representing the neutron image is thereby obtained.

The method for forming a neutron image, wherein a stimulable phosphor sheet is utilized, has the advantages over the neutron radiography where the photographic film and the metal converter are utilized, in that it is possible to form a neutron image having a high sensitivity, a high resolution, and a large area. In addition, that the dose of the neutron beam can be restricted at a low level, and the image signal representing a neutron image can be obtained directly.

A neutron beam has a high penetrating power and readily penetrates through a stimulable phosphor sheet. Therefore, the neutron beam is not readily absorbed by the stimulable phosphor sheet. Such that the neutron beam can be absorbed easily by the stimulable phosphor sheet, it is considered to increase the thickness of the stimulable phosphor sheet. However, for reasons of the transmission of light, which is emitted by the stimulable phosphor sheet when it is exposed to stimulating rays, the thickness of the stimulable phosphor sheet cannot be rendered very thick. At present, the thickness of the stimulable phosphor sheet is limited to at most a value falling within the range of 100 µm to 300 µm.

Therefore, with the conventional method for forming a neutron image wherein a stimulable phosphor sheet is utilized, the efficiency with which a neutron beam is detected cannot be kept high.

In general, neutron beams often contain $\gamma$-rays. Ordinarily, stimulable phosphor sheets have a high sensitivity to $\gamma$-rays. Therefore, when a neutron image is stored on a stimulable phosphor sheet, energy from the $\gamma$-rays contained in the neutron beam is also stored on the stimulable phosphor sheet. In such cases, an image signal detected from the stimulable phosphor sheet also contains components due to the $\gamma$-rays in addition to the image information carried by the neutron beam. Accordingly, it becomes impossible to reproduce an image, which is formed with only the neutron beam, from the image signal.

SUMMARY OF THE INVENTION

The primary object of the present invention is to provide a method for forming a neutron image, wherein the efficiency with which a neutron beam is detected by a stimulable phosphor sheet is kept sufficiently high.

Another object of the present invention is to provide a method for forming a neutron image, wherein adverse effects of $\gamma$-rays contained in a neutron beam are eliminated, and an image signal representing an image, which is formed with only the neutron beam, is obtained.

The present invention provides a first method for forming a neutron image, comprising the steps of:

i) locating a plurality of stimulable phosphor sheets, which are superposed one upon another, each of the stimulable phosphor sheets being provided with a layer of a substance, which is capable of absorbing neutrons and emitting secondary particles, and a layer of a stimulable phosphor, which is capable of storing energy from the secondary particles, ii) exposing the plurality of the stimulable phosphor sheets together to a neutron beam, which carries image information, neutron images being thereby stored on the plurality of the stimulable phosphor sheets, iii) exposing the plurality of the stimulable phosphor sheets, on which the neutron images have been stored, one after another to stimulating rays, which have wavelengths falling within the stimulation wavelength range for the stimulable phosphor of each stimulable phosphor sheet and which cause the stimulable phosphor sheet to emit light in proportion to the amount of energy stored thereon during its exposure to the neutron beam, iv) photoelectrically detecting the light emitted by each of the plurality of the stimulable phosphor sheets, a plurality of image signals, which represent the neutron images stored on the plurality of the stimulable phosphor sheets, being thereby obtained, each image signal being made up of a series of image signal components, and v) adding the image signal components of the plurality of the image signals to one another, which image signal components represent corresponding picture elements in the neutron images, whereby an image signal representing the neutron images stored on the plurality of the stimulable phosphor sheets is obtained.

In the first method for forming a neutron image in accordance with the present invention, the plurality of the stimulable phosphor sheets superposed one upon another may be in contact with one another or may be spaced apart from one another.

In a second method for forming a neutron image in accordance with the present invention, a stimulable phosphor sheet provided with a layer of a substance, which is capable of absorbing neutrons and emitting secondary particles, and a layer of a stimulable phosphor, which is capable of storing energy from the secondary particles, is employed as a neutron beam detecting stimulable phosphor sheet. Also, an ordinary stimulable phosphor sheet, which basically has no capability of detecting a neutron beam, is employed as a γ-ray detecting stimulable phosphor sheet. The neutron beam detecting stimulable phosphor sheet and the γ-ray detecting stimulable phosphor sheet are superposed one upon the other. A calculation process is carried out on image signals, which have been obtained from the neutron beam detecting stimulable phosphor sheet and the γ-ray detecting stimulable phosphor sheet. In this manner, adverse effects of γ-rays are eliminated.

Specifically, the present invention also provides a second method for forming a neutron image, comprising the steps of:

i) locating at least a single neutron beam detecting stimulable phosphor sheet and at least a single γ-ray detecting stimulable phosphor sheet, which are superposed one upon the other, the neutron beam detecting stimulable phosphor sheet being provided with a layer of a substance, which is capable of absorbing neutrons and emitting secondary particles, and a layer of a stimulable phosphor, which is capable of storing energy from the secondary particles, the γ-ray detecting stimulable phosphor sheet being provided with a layer of a stimulable phosphor, which is capable of storing energy from γ-rays, ii) exposing the neutron beam detecting stimulable phosphor sheet and the γ-ray detecting stimulable phosphor sheet together to a neutron beam, which carries image information, images being thereby stored on the neutron beam detecting stimulable phosphor sheet and the γ-ray detecting stimulable phosphor sheet, iii) exposing the neutron beam detecting stimulable phosphor sheet and the γ-ray detecting stimulable phosphor sheet, on which the images have been stored, one after another to stimulating rays, which have wavelengths falling within the stimulation wavelength range for the stimulable phosphor of each stimulable phosphor sheet and which cause the stimulable phosphor sheet to emit light in proportion to the amount of energy stored thereon during its exposure to the neutron beam, iv) photoelectrically detecting the light emitted by each of the neutron beam detecting stimulable phosphor sheet and the γ-ray detecting stimulable phosphor sheet, image signals, which represent the images stored on the neutron beam detecting stimulable phosphor sheet and the γ-ray detecting stimulable phosphor sheet, being thereby obtained, each image signal being made up of a series of image signal components, and v) subtracting the image signal components of the image signal, that has been obtained from the neutron beam detecting stimulable phosphor sheet, and the image signal, that has been obtained from the γ-ray detecting stimulable phosphor sheet, from each other, which image signal components represent corresponding picture elements in the images stored on the neutron beam detecting stimulable phosphor sheet and the γ-ray detecting stimulable phosphor sheet, whereby an image signal approximately representing an image, which is formed with only the neutron beam irradiated to the neutron beam detecting stimulable phosphor sheet, is obtained.

In the second method for forming a neutron image in accordance with the present invention, at least the single neutron beam detecting stimulable phosphor sheet and at least the single γ-ray detecting stimulable phosphor sheet, which are superposed one upon the other, may be in contact with each other or may be spaced apart from each other.

The second method for forming a neutron image in accordance with the present invention should preferably be modified such that a plurality of neutron beam detecting stimulable phosphor sheets and/or a plurality of γ-ray detecting stimulable phosphor sheets may be used, a plurality of image signals, each of which has been obtained by detecting the light emitted by each of the plurality of the neutron beam detecting stimulable phosphor sheets, may be subjected to a superposition process, and/or a plurality of image signals, each of which has been obtained by detecting the light emitted by each of the plurality of the γ-ray detecting stimulable phosphor sheets, may be subjected to a superposition process, and an image signal, which has been obtained from the superposition process carried out on the plurality of image signals detected from the plurality of the neutron beam detecting stimulable phosphor sheets, and/or an image signal, which has been obtained from the superposition process carried out on the plurality of image signals detected from the plurality of the γ-ray detecting stimulable phosphor sheets, may be subjected to the subtraction process.

Stimulable phosphors may be selected from those described in, for example, U.S. Pat. Nos. 3,859,527, 4,236,078, and 4,239,968, DE-OS No. 2,928,245, and Japanese Unexamined Patent Publication Nos. 55(1980)-160078, 56(1981)-116777, 57(1982)-23673, 57(1982)-23675, 58(1983)-69281, 58(1983)-206678, 59(1984)-27980, 59(1984)-47289, 59(1984)-56479, 59(1984)-56480, and 59(1984)-75200.

Examples of the substance which are capable of absorbing neutrons and emitting secondary particles include $^6$Li, $^{10}$B, Gd, Cd, In, Sm, Eu, Dy, and Rh. Among the above-enumerated substances, $^6$Li and $^{10}$B are preferable for the purposes of the present invention. Specifically, $^6$Li absorbs neutrons and emits α-particles of 2.05 MeV and $^3$H particles of 2.74 MeV. Also, $^{10}$B absorbs neutrons and emits α-particles of 1.47 MeV and $^7$Li particles of 0.83 MeV.

With the first method for forming a neutron image in accordance with the present invention, a plurality of stimulable phosphor sheets superposed one upon another are exposed to the neutron beam carrying image information. Therefore, the neutron beam, which has penetrated through a stimulable phosphor sheet, can be absorbed by the next stimulable phosphor sheet. The plurality of the image signals, which have been obtained from image read-out operations carried out on the stimulable phosphor sheets, are added to one another, and an ultimate image signal is thereby obtained. Therefore, the efficiency, with which the neutron beam is detected by the stimulable phosphor sheets, is kept sufficiently high.

The range of the secondary particles, such as $\alpha$-particles and $^3H$ particles, in the stimulable phosphor sheet is at most several tens of microns. Therefore, the problems do not occur in that the secondary particles reach the adjacent stimulable phosphor sheet and the position resolution is thereby rendered low.

With the second method for forming a neutron image in accordance with the present invention, a neutron image is stored with energy from the secondary particles on the neutron beam detecting stimulable phosphor sheet. In cases where $\gamma$-rays are contained in the neutron beam, an image formed with $\gamma$-rays (i.e., a $\gamma$-ray image) is also stored on the neutron beam detecting stimulable phosphor sheet. Also, basically, only the $\gamma$-ray image is stored on the $\gamma$-ray detecting stimulable phosphor sheet. The images signals, which have been obtained from the neutron beam detecting stimulable phosphor sheet and the $\gamma$-ray detecting stimulable phosphor sheet, are weighted, when necessary, with appropriate weight factors and are thereafter subtracted from each other. In this manner, the $\gamma$-ray image components can be canceled in the image signal, which has been obtained from the subtraction process.

In the manner described above, with the second method for forming a neutron image in accordance with the present invention, adverse effects of the $\gamma$-rays contained in the neutron beam can be eliminated, and an image signal representing an image, which is formed with only the neutron beam, can be obtained.

In the second method for forming a neutron image in accordance with the present invention, as in the first method for forming a neutron image in accordance with the present invention, a plurality of neutron beam detecting stimulable phosphor sheets may be used, and the plurality of the image signals detected from the neutron beam detecting stimulable phosphor sheets may be subjected to the superposition process. In this manner, the efficiency, with which the neutron beam is detected, can be kept sufficiently high. Also, a plurality of $\gamma$-ray detecting stimulable phosphor sheets may be used, and the plurality of the image signals detected from the $\gamma$-ray detecting stimulable phosphor sheets may be subjected to the superposition process. In this manner, the efficiency, with which the $\gamma$-rays are detected, can be kept sufficiently high.

The substance $^{10}B$ mentioned above as a preferable example of the substance, which is capable of absorbing neutrons and emitting secondary particles, emits a smaller amount of $\gamma$-rays than the amount emitted by Gd, or the like, when being exposed $\gamma$-ray to a neutron beam. The substance $^6Li$ emits a smaller amount of $\gamma$-rays than the amount emitted by $^{10}B$ when being exposed to a neutron beam.

Therefore, in cases where stimulable phosphor sheets, which contain $^{10}B$ or which more preferably contain $^6Li$, are employed in the first method for forming a neutron image in accordance with the present invention, the problems can be prevented from occurring in that $\gamma$-rays, which are emitted by a stimulable phosphor sheet when the stimulable phosphor sheet is exposed to a neutron beam, are irradiated to this stimulable phosphor sheet or to a different stimulable phosphor sheet, and in that the neutron image, which is stored on this stimulable phosphor sheet or on the different stimulable phosphor sheet, is thereby rendered unsharp.

A stimulable phosphor sheet, which is located on the downstream side with respect to the direction of irradiation of the neutron beam and which is exposed to the neutron beam having penetrated through a plurality of stimulable phosphor sheets, is exposed to more of the $\gamma$-rays than a stimulable phosphor sheet, which is located on the upstream side with respect to the direction of irradiation of the neutron beam. Therefore, the neutron image stored on a stimulable phosphor sheet, which is located on a more downstream side with respect to the direction of irradiation of the neutron beam, becomes more unsharp. For example, in cases where several stimulable phosphor sheets containing Gd as the substance, which is capable of absorbing neutrons and emitting secondary particles, are superposed one upon another and used, the neutron image stored on the stimulable phosphor sheet, which is located on the most downstream side with respect to the direction of irradiation of the neutron beam, becomes markedly unsharp. However, in cases where stimulable phosphor sheets containing $^{10}B$ are used, the degree of unsharpness of the stored neutron image decreases distinctly. In cases where stimulable phosphor sheets containing $^6Li$ are used, the degree of unsharpness of the neutron image stored on the stimulable phosphor sheet, which is located on the most downstream side with respect to the direction of irradiation of the neutron beam, decreases to an extent such that it may be approximately identical with the degree of unsharpness of the neutron image stored on the stimulable phosphor sheet, which is located on the most upstream side with respect to the direction of irradiation of the neutron beam.

In cases where the stimulable phosphor sheet, which contains $^{10}B$ or which more preferably contains $^6Li$, is employed as the neutron beam detecting stimulable phosphor sheet in the second method for forming a neutron image in accordance with the present invention, the adverse effects of the $\gamma$-rays, which are emitted by the stimulable phosphor sheet when the stimulable phosphor sheet is exposed to a neutron beam, can be reduced. Therefore, the neutron image and the $\gamma$-ray image can be appropriately separated from each other, and the neutron image having good image quality and a high signal-to-noise ratio can be formed.

Further, with the first and second methods for forming a neutron image in accordance with the present invention, a neutron image is stored on the stimulable phosphor sheet containing the substance, which is capable of absorbing neutrons and emitting secondary particles. Therefore, various advantages of the use of such a stimulable phosphor sheet can be obtained, and an image signal representing a neutron image having a high sensitivity, a high resolution, and a large area obtained.

DESCRIPTION OF THE PREFERRED EMBODIMENTS

The present invention will hereinbelow be described in further detail with reference to the accompanying drawings.

Figure 1:
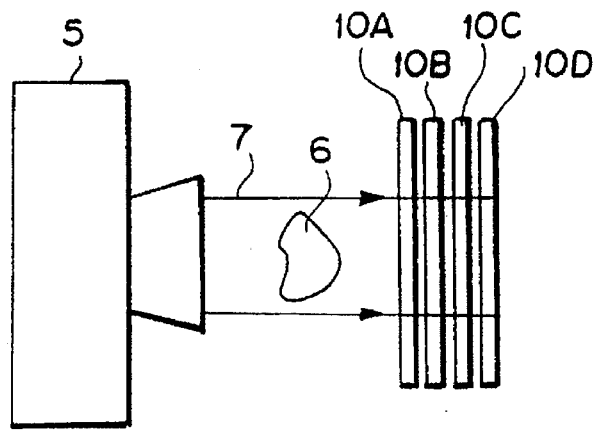
FIG. 1 is a schematic view showing how neutron images are recorded on a plurality of stimulable phosphor sheets in a first embodiment of the method for forming a neutron image in accordance with the present invention.
Figure 2:
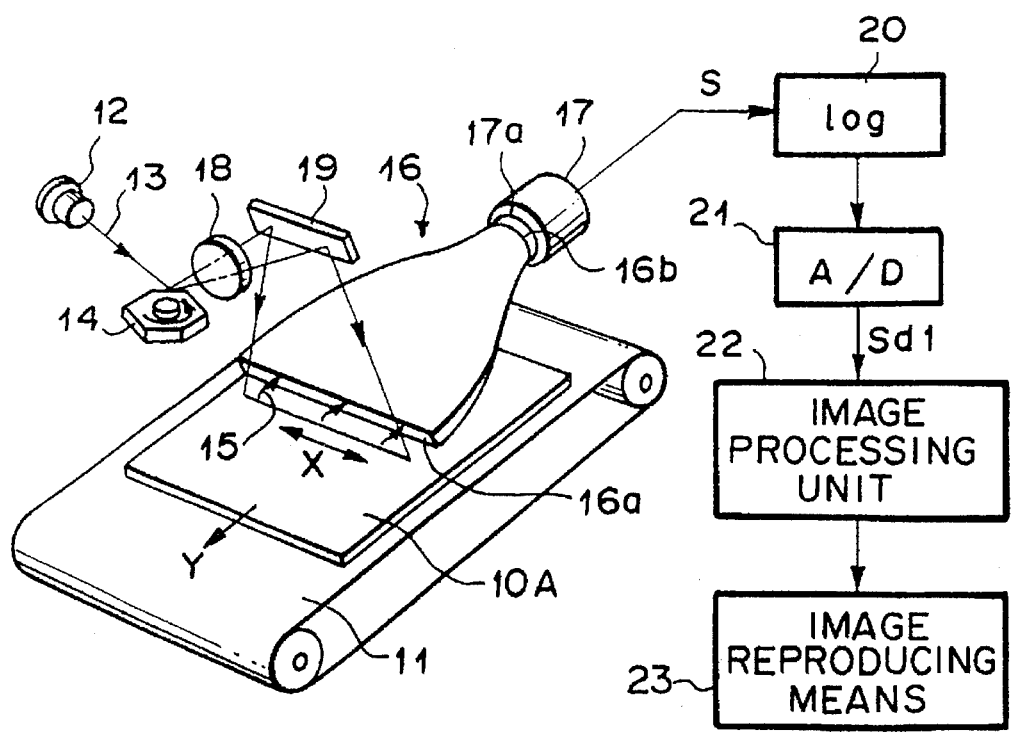
FIG. 2 is a perspective view showing how a neutron image is read out from a stimulable phosphor sheet in the first embodiment of the method for forming a neutron image in accordance with the present invention.
Figure 3:
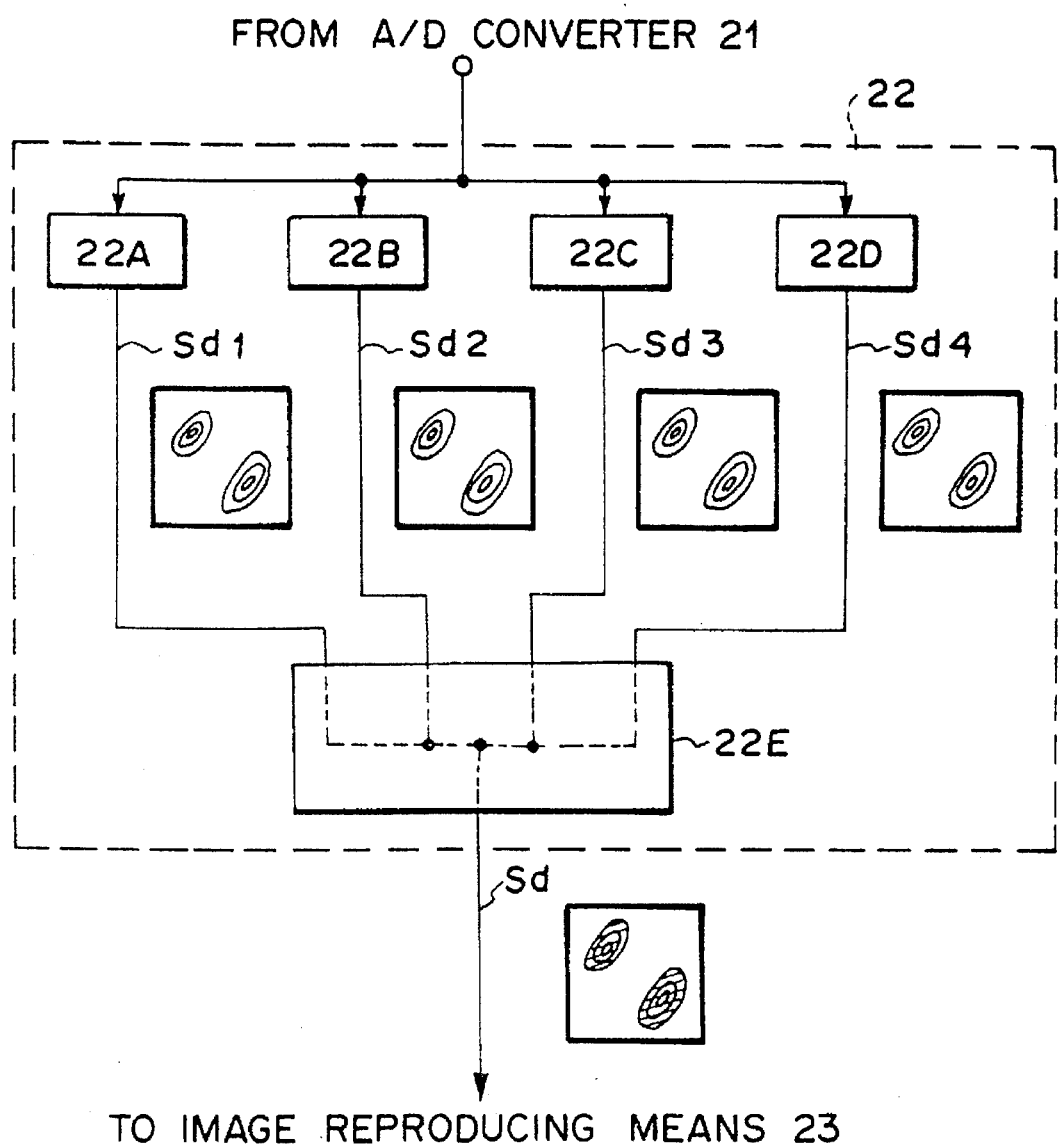
FIG. 3 is a block diagram showing how a superposition process is carried out in the first embodiment of the method for forming a neutron image in accordance with the present invention.

FIG. 1 is a schematic view showing how neutron images are recorded on a plurality of stimulable phosphor sheets in a first embodiment of the method for forming a neutron image in accordance with the present invention. FIG. 2 is a perspective view showing how a neutron image is read out from a stimulable phosphor sheet in the first embodiment of the method for forming a neutron image in accordance with the present invention. FIG. 3 is a block diagram showing how a superposition process is carried out in the first embodiment of the method for forming a neutron image in accordance with the present invention.

As illustrated in FIG. 1, a neutron beam 7 is produced by a neutron generator 5 and irradiated to an object 6. Four stimulable phosphor sheets 10A, 10B, 10C, and 10D, which are capable of detecting a neutron beam, are superposed one upon another. The stimulable phosphor sheets 10A, 10B, 10C, and 10D are located at the position that is exposed to the neutron beam 7, which has passed through the object 6.

The neutron generator 5 may be selected from known neutron generating apparatuses, such as a nuclear reactor utilizing a nuclear fission reaction of enriched uranium, or the like, a high energy accelerator, and an apparatus utilizing spontaneous nuclear fission of $^{252}$Cf.

Figure 4:
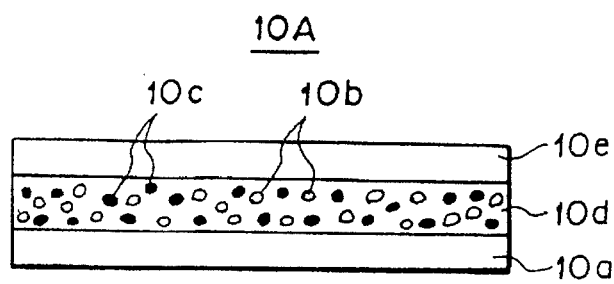
FIG. 4 is a sectional side view showing an example of a neutron beam detecting stimulable phosphor sheet, which may be employed in the method for forming a neutron image in accordance with the present invention.

As illustrated in FIG. 4, the stimulable phosphor sheet 10A comprises a sheet-shaped substrate 10a, a layer 10d containing a substance 10b, which is capable of absorbing neutrons and emitting secondary particles, and a stimulable phosphor 10c, and a protective layer 10e. The layer 10d and the protective layer 10e are overlaid in this order on the substrate 10a. The stimulable phosphor 10c and the substance 10b, which is capable of absorbing neutrons and emitting secondary particles, may be selected from the substances enumerated above. In this embodiment, in particular, a BaFBr:Eu phosphor is employed as the stimulable phosphor 10c, and $^{6}$Li is employed as the substance 10b, which is capable of absorbing neutrons and emitting secondary particles. Particles of the BaFBr:Eu phosphor and particles of $^{6}$Li are mixed together in a weight ratio of 1:1 and dispersed in a binder. In this manner, the layer 10d having a thickness of 200 μm is formed. In order for the layer 10d to be formed, one of various processes disclosed in Japanese Unexamined Patent Publication No. 61(1986)-28899 may be employed.

The other three stimulable phosphor sheets 10B, 10C, and 10D have the same structure as the structure of the stimulable phosphor sheet 10A.

Figure 5:
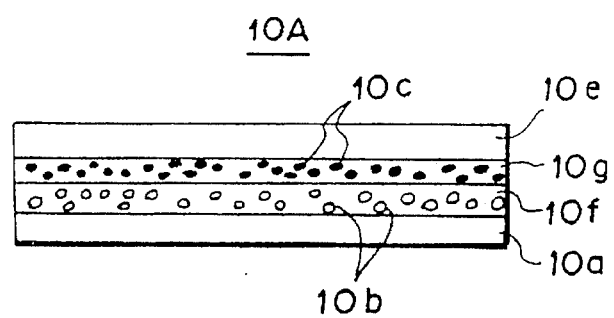
FIG. 5 is a sectional side view showing a different example of a neutron beam detecting stimulable phosphor sheet, which may be employed in the method for forming a neutron image in accordance with the present invention.

In this embodiment, as described above, particles of the substance 10b, which is capable of absorbing neutrons and emitting secondary particles, and particles of the stimulable phosphor 10c are dispersed in the single layer 10d. Alternatively, as illustrated in FIG. 5, a layer 10f, which contains the substance 10b dispersed therein, and a layer 10g, which contains the stimulable phosphor 10c dispersed therein, may be formed independently of each other, and the stimulable phosphor sheet 10A may thereby be constituted. The substrate 10a may be omitted in cases where the layer 10d has the self-supporting properties, or the layer 10f and/or the layer 10g has the self-supporting properties.

The neutron beam 7, which has passed through the object 6, has the energy distribution in accordance with the transmittance of each of various portions of the object 6 with respect to the neutron beam. The neutron beam 7, which thus carries the image information of the object 6, impinges upon the stimulable phosphor sheet 10A and is absorbed by the layer 10d of the stimulable phosphor sheet 10A. Part of the neutron beam 7 penetrates through the stimulable phosphor sheet 10A and impinges upon the next stimulable phosphor sheet 10B. In the same manner as that described above, the neutron beam 7 also impinges upon the other stimulable phosphor sheets 10C and 10D.

The neutron beam 7 has a high penetrating power, and therefore it is not always possible for the thin layer 10d of each of the stimulable phosphor sheets 10A, 10B, 10C, and 10D to absorb a large amount of the neutron beam 7. However, in this embodiment, the neutron beam 7 is irradiated successively to the four stimulable phosphor sheets 10A, 10B, 10C, and 10D. Therefore, a total of a large amount of the neutron beam 7 can be absorbed by the set of the stimulable phosphor sheets 10A, 10B, 10C, and 10D.

When the neutron beam 7 is irradiated to the stimulable phosphor sheets 10A, 10B, 10C, and 10D in the manner described above, the neutron beam 7 is absorbed by $^{6}$Li, which is contained in the layer 10d of each of the stimulable phosphor sheets 10A, 10B, 10C, and 10D. The neutron beam 7 is converted by $^{6}$Li into secondary particles, such as α-particles and $^{3}$H particles. Energy from the secondary particles is stored in the stimulable phosphor 10c. In the manner described above, a neutron image of the object 6 is recorded as a latent image with energy from the secondary particles on each of the stimulable phosphor sheets 10A, 10B, 10C, and 10D.

Thereafter, each of the stimulable phosphor sheets 10A, 10B, 10C, and 10D, on which the neutron images have been stored, is subjected to a neutron image read-out operation, which is carried out with an apparatus shown in FIG. 2. By way of example, how the neutron image is read out from the stimulable phosphor sheet 10A will be described hereinbelow.

With reference to FIG. 2, the stimulable phosphor sheet 10A is conveyed in a sub-scanning direction, which is indicated by the arrow Y, by a sheet conveyance means 11, which may be constituted of an endless belt, or the like. A laser beam 13, which serves as stimulating rays, is produced by a laser beam source 12. The laser beam 13 is reflected and deflected by a rotating polygon mirror 14, which is being rotated quickly. The laser beam 13 is then converged by a scanning lens 18, which may be constituted of an fθ lens, or the like. The laser beam 13 is then reflected by a mirror 19. In this manner, the laser beam 13 is caused to impinge upon the stimulable phosphor sheet 10A and scan it in main scanning directions indicated by the double headed arrow X. The main scanning directions are approximately normal to the sub-scanning direction indicated by the arrow Y.

When the stimulable phosphor sheet 10A is exposed to the laser beam 13, the exposed portion of the stimulable phosphor sheet 10A emits light 15 in an amount proportional to the amount of energy stored thereon during its exposure to the neutron beam. The emitted light 15 is guided by a light guide member 16 and photoelectrically detected by a photomultiplier 17, which serves as a photodetector.

As the laser beam source 12, a device capable of producing the laser beam 13 having a wavelength of 633 nm, which is close to the stimulation peak wavelength for the stimulable phosphor 10c, is employed. A filter 17a is located such that it may be in close contact with a light receiving face of the photomultiplier 17. The filter 17a filters out the light having wavelengths (e.g., of 500 nm or longer) which are longer than the primary wavelength range of the light emitted by the stimulable phosphor 10c. Therefore, the photomultiplier 17 can detect only the emitted light 15 without the laser beam 13 being detected.

The light guide member 16 is made from a light guiding material, such as an acrylic plate. The light guide member 16 has a linear light input face 16a, positioned to extend along the main scanning line on the stimulable phosphor sheet 10A, and a ring-shaped light output face 16b, positioned so that it is in close contact with the light receiving face of the photomultiplier 17. The emitted light 15, which has entered the light guide member 16 from its light input face 16a, is guided through repeated total reflection inside of the light guide member 16, emanates from the light output face 16b, and is received by the photomultiplier 17. In this manner, the amount of the emitted light 15, which amount represents the neutron image stored on the stimulable phosphor sheet 10A, is converted into an electric signal by the photomultiplier 17.

An analog output signal (i.e., an image signal) S generated by the photomultiplier 17 is logarithmically amplified by a logarithmic amplifier 20, and fed into an analog-to-digital converter 21. The analog-to-digital converter 21 samples the analog signal S, and the sampled signal is converted into a digital image signal Sd1 with a predetermined scale factor. The digital image signal Sd1 thus obtained is fed into an image processing unit 22 and subjected to an addition process (i.e., a superposition process).

How the addition process is carried out will be described hereinbelow with reference to FIG. 3. In the same manner as that described above, in the apparatus shown in FIG. 2, the image read-out operation is carried out on each of the other three stimulable phosphor sheets 10B, 10C, and 10D. Digital image signals Sd2, Sd3, and Sd4 are thereby obtained from the three stimulable phosphor sheets 10B, 10C, and 10D and fed into the image processing unit 22.

The digital image signals Sd1, Sd2, Sd3, and Sd4 are respectively stored in image files 22A, 22B, 22C, and 22D of the image processing unit 22. Thereafter, the digital image signals Sd1, Sd2, Sd3, and Sd4 are read from the image files 22A, 22B, 22C, and 22D and fed into an operation means 22E. In the operation means 22E, the image signal components of the digital image signals Sd1, Sd2, Sd3, and Sd4 are added to one another, which image signal components represent corresponding picture elements in the neutron images. In this manner, a digital image signal Sd is obtained. As illustrated in FIG. 2, the digital image signal Sd is fed into an image reproducing means 23, which may be constituted of a cathode ray tube display device (CRT display device), a light beam scanning recording apparatus, or the like. In the image reproducing means 23, the neutron image of the object 6 is reproduced as a visible image from the digital image signal Sd.

As described above, it is not always possible for each of the stimulable phosphor sheets 10A, 10B, 10C, and 10D to absorb a large amount of the neutron beam 7. However, in this embodiment, the digital image signal Sd is obtained from the total amount of the neutron beam 7, which was absorbed by the four stimulable phosphor sheets 10A, 10B, 10C, and 10D. Therefore, the efficiency, with which the neutron beam 7 is detected, can be kept high, and a neutron image having a high signal-to-noise ratio can be reproduced from the digital image signal Sd.

In this embodiment, the stimulable phosphor sheets 10A, 10B, 10C, and 10D containing $^6$Li as the substance, which is capable of absorbing neutrons and emitting secondary particles, are employed. When being exposed to a neutron beam, $^6$Li emits only a small amount of γ-rays. Therefore, the problems can be prevented from occurring in that the neutron images stored on the stimulable phosphor sheets 10A, 10B, 10C, and 10D become unsharp due to the γ-rays. If a large amount of γ-rays are produced by the substance, which is capable of absorbing neutrons and emitting secondary particles, the neutron image stored on a stimulable phosphor sheet, which is located on a more downstream side with respect to the direction of irradiation of the neutron beam 7, will become more unsharp. However, in this embodiment, wherein the stimulable phosphor sheets 10A, 10B, 10C, and 10D containing $^6$Li are used, the degree of unsharpness of the neutron image stored on the stimulable phosphor sheet 10D, which is located on the most downstream side with respect to the direction of irradiation of the neutron beam 7, decreases to an extent such that it may be approximately identical with the degree of unsharpness of the neutron image stored on the stimulable phosphor sheet 10A, which is located on the most upstream side with respect to the direction of irradiation of the neutron beam.

Image processing, such as gradation processing or frequency processing, which has heretofore been known, may be carried out on the digital image signals Sd1, Sd2, Sd3, and Sd4 before being subjected to the superposition process or on the digital image signal Sd, which has been obtained from the superposition process.

After the digital image signals Sd1, Sd2, Sd3, and Sd4 have been detected from the stimulable phosphor sheets 10A, 10B, 10C, and 10D, the stimulable phosphor sheets 10A, 10B, 10C, and 10D may be exposed to erasing light, which has wavelengths falling within the stimulation wavelength range for the stimulable phosphor, or may be heated. In this manner, energy remaining on the stimulable phosphor sheets 10A, 10B, 10C, and 10D may be released. In cases where such an erasing operation is carried out, when each stimulable phosphor sheet is again used to record a neutron image, noise due to energy remaining on the stimulable phosphor sheet can be restricted.

Before the aforesaid operation (a final readout) for reading out the neutron image stored on each of the stimulable phosphor sheets 10A, 10B, 10C, and 10D is carried out, a preliminary readout for approximately ascertaining the stored neutron image information may be carried out. Such a preliminary readout is described in, for example, Japanese Unexamined Patent Publication No. 61(1986)-156250. Read-out conditions, under which the final readout is carried out, and image processing conditions, under which an image signal is processed, may then be adjusted appropriately in accordance with the ascertained neutron image information.

In this embodiment, the four stimulable phosphor sheets 10A, 10B, 10C, and 10D are used in order to detect the neutron beam 7. However, the number of the neutron beam detecting stimulable phosphor sheets is not limited to four, and may be at least two.

Figure 6:
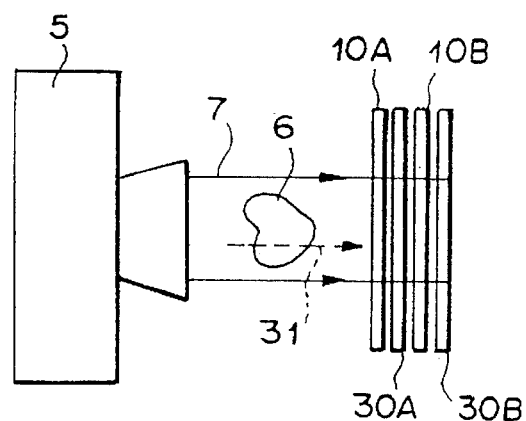
FIG. 6 is a schematic view showing how neutron images are recorded on stimulable phosphor sheets in a second embodiment of the method for forming a neutron image in accordance with the present invention.
Figure 7:
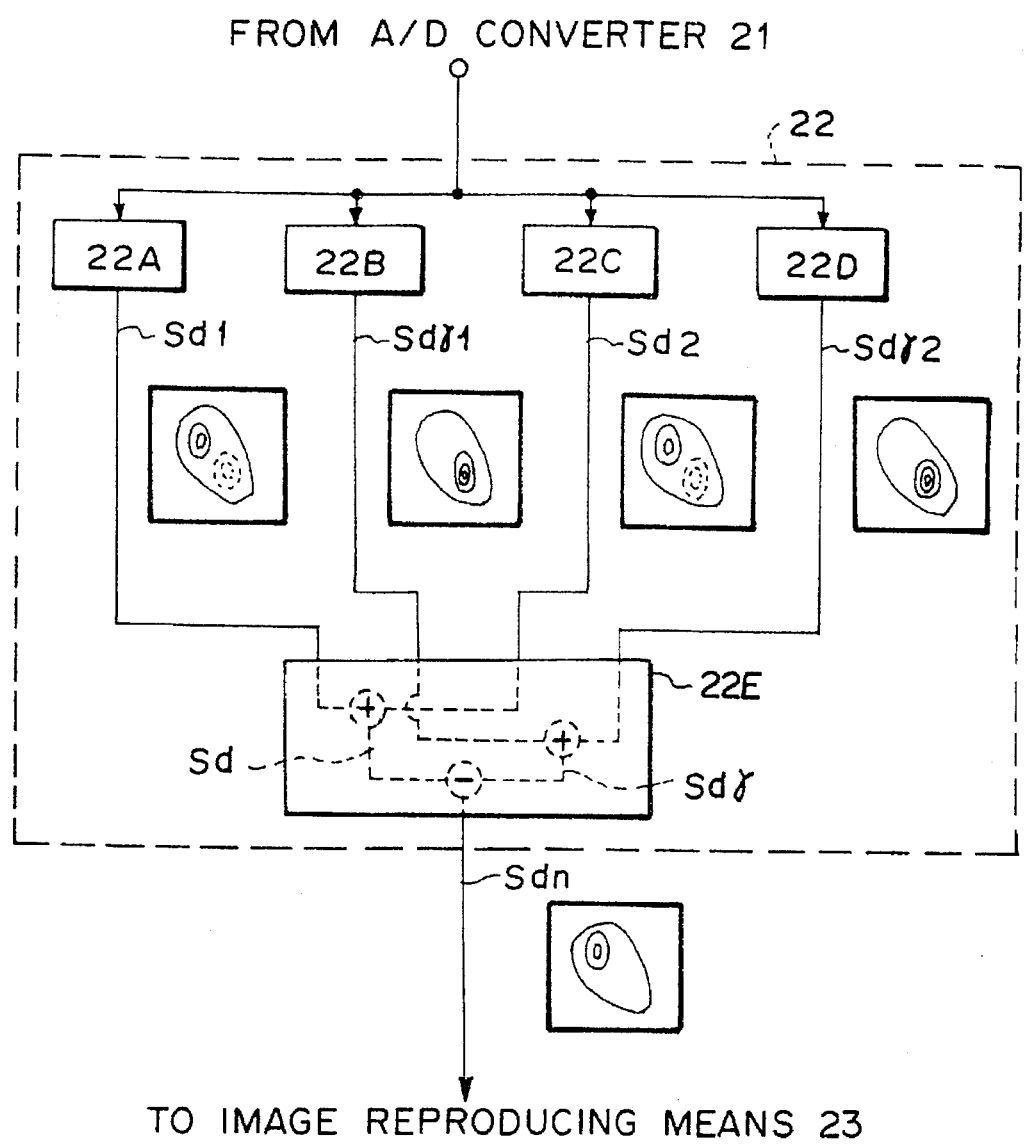
FIG. 7 is a block diagram showing how a subtraction process is carried out in the second embodiment of the method for forming a neutron image in accordance with the present invention.

A second embodiment of the method for forming a neutron image in accordance with the present invention will be described hereinbelow. FIG. 6 is a schematic view showing how neutron images are recorded on stimulable phosphor sheets in the second embodiment of the method for forming a neutron image in accordance with the present invention. FIG. 7 is a block diagram showing how a subtraction process is carried out in the second embodiment of the method for forming a neutron image in accordance with the present invention. In FIGS. 6 and 7, similar elements are numbered with the same reference numerals with respect to FIGS. 1 and 3.

As illustrated in FIG. 6, two stimulable phosphor sheets (i.e., neutron beam detecting stimulable phosphor sheets) 10A and 10B, which are capable of detecting a neutron beam, and two γ-ray detecting stimulable phosphor sheets 30A and 30B, which are basically not capable of detecting a neutron beam, are superposed one upon another. The neutron beam detecting stimulable phosphor sheets 10A and 10B and the γ-ray detecting stimulable phosphor sheets 30A and 30B are located at the position that is exposed to the neutron beam 7, which has passed through the object 6. In this embodiment, neutron beam detecting stimulable phosphor sheets 10A and 10B and the γ-ray detecting stimulable phosphor sheets 30A and 30B are alternately located.

Figure 8:
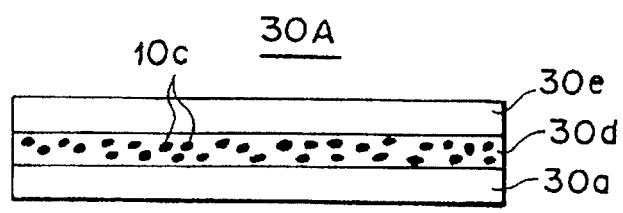
FIG. 8 is a sectional side view showing an example of a γ-ray detecting stimulable phosphor sheet, which may be employed in the method for forming a neutron image in accordance with the present invention.

As illustrated in FIG. 8, the γ-ray detecting stimulable phosphor sheet 30A comprises a sheet-shaped substrate 30a, a layer 30d containing the stimulable phosphor 10c, and a protective layer 30e. The layer 30d and the protective layer 30e are overlaid in this order on the substrate 30a. Specifically, the γ-ray detecting stimulable phosphor sheet 30A is basically different from the stimulable phosphor sheets 10A, 10B, 10C, and 10D in that the γ-ray detecting stimulable phosphor sheet 30A does not contain the substance 10b, which is capable of absorbing neutrons and emitting secondary particles. The other γ-ray detecting stimulable phosphor sheet 30B has the same structure as the structure of the γ-ray detecting stimulable phosphor sheet 30A.

The neutron beam 7, which has passed through the object 6 and now carries the image information of the object 6, is absorbed by the neutron beam detecting stimulable phosphor sheets 10A and 10B. As a result, on the neutron beam detecting stimulable phosphor sheets 10A and 10B, neutron images of the object 6 are recorded as latent images with energy from the secondary particles produced by the substance 10b.

As described above, in cases where γ-rays 31 are contained in the neutron beam 7, the γ-rays 31 are absorbed by the stimulable phosphor 10c of each of the neutron beam detecting stimulable phosphor sheets 10A and 10B. The image information formed with the γ-rays 31 adversely affects the image, appearing as noise upon the formation of an image of the object 6, which image is formed only with the neutron beam 7.

The γ-rays 31 also impinge upon the γ-ray detecting stimulable phosphor sheets 30A and 30B and are absorbed by the stimulable phosphor 10c of each of the γ-ray detecting stimulable phosphor sheets 30A and 30B. As a result, γ-ray images of the object 6 are stored on the γ-ray detecting stimulable phosphor sheets 30A and 30B.

The operation for recording the neutron images is carried out in the manner described above. Thereafter, in the apparatus shown in FIG. 2, the image read-out operation is carried out on each of the neutron beam detecting stimulable phosphor sheets 10A and 10B and the γ-ray detecting stimulable phosphor sheets 30A and 30B. The image read-out operation is carried out in the same manner as that in the first embodiment. In this manner, the digital image signals Sd1 and Sd2 are obtained from the image read-out operations carried out on the neutron beam detecting stimulable phosphor sheets 10A and 10B. Also, digital image signals Sdγ1 and Sdγ2 are obtained from the image read-out operations carried out on the γ-ray detecting stimulable phosphor sheets 30A and 30B. The digital image signals Sd1 and Sd2 and the digital image signals Sdγ1 and Sdγ2 are fed into the image processing unit 22.

As illustrated in FIG. 7, the digital image signals Sd1 and Sd2 are respectively stored in the image files 22A and 22C of the image processing unit 22. The digital image signals Sdγ1 and Sdγ2 are respectively stored in the image files 22B and 22D of the image processing unit 22. Thereafter, the digital image signals Sd1 and Sd2 and the digital image signals Sdγ1 and Sdγ2 are read from the image files 22A, 22C, 22B, and 22D. In the operation means 22E, the digital image signals Sd1 and Sd2 are added to each other, and a digital image signal Sd is thereby obtained. Also, the digital image signals Sdγ1 and Sdγ2 are added to each other, and a digital image signal Sdγ is thereby obtained. Thereafter, the image signal components of the digital image signals Sd and Sdγ are weighted and subtracted from each other, which image signal components represent corresponding picture elements in the images.

Specifically, the calculation is carried out with the formula $$Sdn = Sd - c \cdot Sd\gamma$$

wherein c represents a fixed number. In this manner, a digital image signal Sdn is obtained. The digital image signal Sdn is fed into the image reproducing means 23, which is shown in FIG. 2 and may be constituted of a CRT display device, a light beam scanning recording apparatus, or the like. In the image reproducing means 23, the neutron image of the object 6 is reproduced as a visible image from the digital image signal Sdn.

The digital image signal Sdn described above represents the image formed with the neutron beam 7 and the γ-rays 31. The digital image signal Sdγ represents the image formed with the γ-rays 31. Therefore, in cases where the fixed number c is determined appropriately and the subtraction process is carried out with the formula shown above, the components due to the γ-rays 31 can be eliminated in the digital image signal Sdn, which has been obtained from the subtraction process. Accordingly, when the digital image signal Sdn is used, the image of the object 6 formed with only the neutron beam 7 can be reproduced.

In the second embodiment, the neutron beam detecting stimulable phosphor sheets 10A and 10B containing $^6$Li as the substance, which is capable of absorbing neutrons and emitting secondary particles, are employed. When being exposed to a neutron beam, $^6$Li emits only a small amount of γ-rays. Therefore, the neutron image and the γ-ray image can be appropriately separated from each other, and the neutron image having good image quality and a high signal-to-noise ratio can be formed.

Also, in the second embodiment, the two stimulable phosphor sheets 10A and 10B are employed for the detection of the neutron beam 7, and the digital image signals Sd1 and Sd2, which have been obtained from the two neutron beam detecting stimulable phosphor sheets 10A and 10B, are superposed one upon the other. Therefore, as in the first embodiment, the efficiency, with which the neutron beam 7 is detected, can be kept high. Also, in the second embodiment, the two γ-ray detecting stimulable phosphor sheets 30A and 30B are employed, and the digital image signals Sdγ1 and Sdγ2, which have been obtained from the two γ-ray detecting stimulable phosphor sheets 30A and 30B, are superposed one upon the other. Therefore, the efficiency, with which the γ-rays are detected, can be kept high.

Further, in the second embodiment, the two neutron beam detecting stimulable phosphor sheets 10A and 10B and the two γ-ray detecting stimulable phosphor sheets 30A and 30B are employed. However, the number of the neutron beam detecting stimulable phosphor sheets is not limited to two, and may be at least one. Also, the number of the γ-ray detecting stimulable phosphor sheets is not limited to two, and may be at least one.

In the two embodiments described above, a stimulable phosphor sheet is exposed to the neutron beam 7, which has passed through the object 6, and the neutron image of the object 6 is thereby stored on the stimulable phosphor sheet. The method for forming a neutron image in accordance with the present invention is also applicable when a stimulable phosphor sheet is exposed to a neutron beam, which has been emitted by a sample, and a neutron image of the sample is thereby stored on the stimulable phosphor sheet.

Moreover, in the embodiments described above, a single still image is reproduced. However, the method for forming a neutron image in accordance with the present invention is applicable broadly when images are formed with neutron beams as in three-dimensional imaging, formation of neutron diffraction images, and the like.

What is claimed is:

1. A method for forming a neutron image, comprising the steps of:

i) locating at least one neutron beam detecting stimulable phosphor sheet and at least one γ-ray detecting stimulable phosphor sheet, which are superposed one upon the other, the neutron beam detecting stimulable phosphor sheet being provided with a layer of a substance, which is capable of absorbing neutrons and emitting secondary particles, and a layer of a stimulable phosphor, which is capable of storing energy from the secondary particles, the γ-ray detecting stimulable phosphor sheet being provided with a layer of a stimulable phosphor, which is capable of storing energy from γ-rays, ii) exposing the neutron beam detecting stimulable phosphor sheet and the γ-ray detecting stimulable phosphor sheet to a neutron beam, which carries image information to store images on the neutron beam detecting stimulable phosphor sheet and the γ-ray detecting stimulable phosphor sheet, iii) sequentially exposing the neutron beam detecting stimulable phosphor sheet and the γ-ray detecting stimulable phosphor sheet, on which the images have been stored, to stimulating rays, which have wavelengths falling within a stimulation wavelength range for the stimulable phosphor of each stimulable phosphor sheet and which cause each stimulable phosphor sheet to emit light in proportion to an amount of energy stored thereon during its exposure to the neutron beam, iv) photoelectrically detecting light emitted by each of the neutron beam detecting stimulable phosphor sheet and the γ-ray detecting stimulable phosphor sheet as image signals, which represent the images stored on the neutron beam detecting stimulable phosphor sheet and the γ-ray detecting stimulable phosphor sheet, wherein each image signal comprises a series of image signal components, and v) subtracting the image signal components of the image signal, that has been obtained from the neutron beam detecting stimulable phosphor sheet, and the image signal components of the image signal, that has been obtained from the γ-ray detecting stimulable phosphor sheet, from each other, wherein said image signal components represent corresponding picture elements in the images stored on the neutron beam detecting stimulable phosphor sheet and the γ-ray detecting stimulable phosphor sheet, to obtain an image signal approximately representing an image, which is formed with only the neutron beam irradiated to the neutron beam detecting stimulable phosphor sheet.

2. A method as defined in claim 1, wherein a plurality of neutron beam detecting stimulable phosphor sheets and a plurality of γ-ray detecting stimulable phosphor sheets are used, a plurality of image signals, each of which has been obtained by detecting the light emitted by each of the plurality of neutron beam detecting stimulable phosphor sheets, are subjected to a superposition step, and a plurality of image signals, each of which has been obtained by detecting the light emitted by each of the plurality of γ-ray detecting stimulable phosphor sheets, are subjected to a superposition step, and an image signal, which has been obtained from the superposition step carried out on the plurality of image signals detected from the plurality of the neutron beam detecting stimulable phosphor sheets, and an image signal, which has been obtained from the superposition step carried out on the plurality of image signals detected from the plurality of the γ-ray detecting stimulable phosphor sheets, is subjected to the subtracting step.

3. A method as defined in claim 2 wherein said substance, which is capable of absorbing neutrons and emitting secondary particles, comprises at least one of $^6$Li and $^{10}$B.

4. A method as defined in claim 1 wherein said substance, which is capable of absorbing neutrons and emitting secondary particles, comprises at least one of $^6$Li and $^{10}$B.

5. A method as defined in claim 1, 2, 4 or 3 wherein said layer of said substance, which is capable of absorbing neutrons and emitting secondary particles, and said layer of said stimulable phosphor, which is capable of storing energy from the secondary particles, are independent of each other.

6. A method as defined in claim 1, 2, 4 or 3 wherein said substance, which is capable of absorbing neutrons and emitting secondary particles, and said stimulable phosphor, which is capable of storing energy from the secondary particles, are dispersed in a single layer, and said single layer serves both as said layer of said substance, which is capable of absorbing neutrons and emitting secondary particles, and as said layer of said stimulable phosphor, which is capable of storing energy from the secondary particles.

7. A method as defined in claim 1, wherein a plurality of neutron beam detecting stimulable phosphor sheets are used, a plurality of image signals, each of which has been obtained by detecting the light emitted by each of the plurality of neutron beam detecting stimulable phosphor sheets, are subjected to a superposition step, and an image signal, which has been obtained from the superposition step carried out on the plurality of image signals detected from the plurality of neutron beam detecting stimulable phosphor sheets, is subjected to the subtracting step.

8. A method as defined in claim 1, wherein a plurality of γ-ray detecting stimulable phosphor sheets are used, a plurality of image signals, each of which has been obtained by detecting the light emitted by each of the plurality of γ-ray detecting stimulable phosphor sheets, are subjected to a superposition step, and an image signal, which has been obtained from the superposition step carried out on the plurality of image signals detected from the plurality of γ-ray detecting stimulable phosphor sheets, is subjected to the subtracting step.

9. A method as defined in claim 7 or 8, wherein said substance, which is capable of absorbing neutrons and emitting secondary particles, comprises at least one of $^6$Li and $^{10}$B.

10. A method as defined in claim 7 or 8, wherein said layer of said substance, which is capable of absorbing neutrons and emitting secondary particles, and said layer of said stimulable phosphor, which is capable of storing energy from the secondary particles, are independent of each other.

11. A method as defined in claim 7 or 8, wherein said substance, which is capable of absorbing neutrons and emitting secondary particles, and said stimulable phosphor, which is capable of storing energy from the secondary particles, are dispersed in a single layer, and said single layer serves both as said layer of said substance, which is capable of absorbing neutrons and emitting secondary particles, and as said layer of said stimulable phosphor, which is capable of storing energy from the secondary particles.

* * * * *